United States Patent
Dimson et al.

(10) Patent No.: US 10,094,746 B2
(45) Date of Patent: Oct. 9, 2018

(54) SAMPLE EXTRACTION APPARATUS WITH MICRO ELUTION BED DESIGN

(71) Applicant: SPEware Corporation, Baldwin Park, CA (US)

(72) Inventors: Philip A. Dimson, San Pedro, CA (US); Bruce Redmond, Claremont, CA (US)

(73) Assignee: TECAN SP, INC., Baldwin Park, CA (US)

( * ) Notice: Subject to any disclaimer, the term of this patent is extended or adjusted under 35 U.S.C. 154(b) by 0 days.

(21) Appl. No.: 14/718,065

(22) Filed: May 20, 2015

(65) Prior Publication Data
US 2015/0338317 A1    Nov. 26, 2015

Related U.S. Application Data

(60) Provisional application No. 62/000,759, filed on May 20, 2014.

(51) Int. Cl.
| | | |
|---|---|---|
| *G01N 1/10* | (2006.01) | |
| *G01N 33/74* | (2006.01) | |
| *G01N 33/493* | (2006.01) | |

(52) U.S. Cl.
CPC .............. *G01N 1/10* (2013.01); *G01N 33/74* (2013.01); *G01N 33/493* (2013.01)

(58) Field of Classification Search
CPC .............................................. G01N 2030/065
See application file for complete search history.

(56) References Cited

U.S. PATENT DOCUMENTS

| | | | | | |
|---|---|---|---|---|---|
| 3,935,111 | A | * | 1/1976 | Bentley | A61M 5/165 210/446 |
| 5,039,419 | A | * | 8/1991 | Bradshaw | C07F 7/1836 210/198.2 |
| 5,057,426 | A | * | 10/1991 | Henco | C12N 15/101 435/270 |
| 5,368,729 | A | * | 11/1994 | Stefkovich | B01D 15/00 210/266 |
| 5,595,653 | A |   | 1/1997 | Good et al. | |

(Continued)

OTHER PUBLICATIONS

International Search Report and Written Opinion, PCT/US2015/031858, dated Aug. 12, 2015.

(Continued)

*Primary Examiner* — Harshad R Patel
*Assistant Examiner* — Tran M Tran
(74) *Attorney, Agent, or Firm* — Entralta P.C.; Justin G. Sanders; Peter D. Weinstein

(57) ABSTRACT

An apparatus for extracting an analyte from a liquid sample having a container with an entrance, an exit, and a passage therebetween for passage of a liquid sample containing an analyte, the container having a full diameter bed region and a reduced diameter bed region. The container includes a layered construction extending across the passage, having from top to bottom: (i) an upper flow distributor/support layer, (ii) an upper compression layer, (iii) an extraction layer of microparticulate extraction medium adjacent to the layer (ii), and (iv) a lower compression layer located adjacent to the extraction layer (iii). At least some of the layers are located in the full diameter bed region, and some of the layers are located in the reduced diameter bed region.

16 Claims, 9 Drawing Sheets

(56) References Cited

U.S. PATENT DOCUMENTS

| | | | | |
|---|---|---|---|---|
| 5,658,800 A * | 8/1997 | Lessard | | G01N 30/06 |
| | | | | 210/634 |
| 5,660,173 A * | 8/1997 | Newton | | A62B 23/02 |
| | | | | 128/205.27 |
| 6,020,186 A * | 2/2000 | Henco | | C12N 15/1006 |
| | | | | 210/266 |
| 6,277,648 B1 * | 8/2001 | Colpan | | B01D 39/00 |
| | | | | 210/489 |
| 6,530,288 B1 * | 3/2003 | August | | G01N 1/405 |
| | | | | 73/863.31 |
| 6,609,618 B2 * | 8/2003 | Colpan | | B01D 39/00 |
| | | | | 210/488 |
| 7,556,733 B2 * | 7/2009 | Smith | | B01L 3/5021 |
| | | | | 210/240 |
| 7,749,388 B2 * | 7/2010 | Pai | | B01L 3/5021 |
| | | | | 210/656 |
| 7,943,393 B2 | 5/2011 | Gjerde et al. | | |
| 8,101,073 B2 * | 1/2012 | Wada | | B01J 20/26 |
| | | | | 210/198.2 |
| 8,247,545 B1 * | 8/2012 | Colpan | | B01D 39/00 |
| | | | | 536/25.4 |
| 8,263,390 B2 * | 9/2012 | Tajima | | B01L 3/0275 |
| | | | | 422/405 |
| 8,518,347 B2 * | 8/2013 | Tajima | | B01D 15/22 |
| | | | | 422/501 |
| 8,562,840 B2 * | 10/2013 | Dawson | | G01N 30/6052 |
| | | | | 210/651 |
| 9,005,436 B2 * | 4/2015 | Linford | | B01J 13/02 |
| | | | | 210/198.2 |
| 9,101,921 B2 * | 8/2015 | Tajima | | B01D 15/22 |
| 9,227,173 B2 * | 1/2016 | Leach | | B01D 15/00 |
| 9,358,494 B2 * | 6/2016 | Frankel | | B01D 53/0415 |
| 2002/0151086 A1 * | 10/2002 | Hage | | G01N 33/54313 |
| | | | | 436/516 |
| 2005/0258097 A1 | 11/2005 | Gjerde et al. | | |
| 2007/0102358 A1 * | 5/2007 | Good | | B01J 20/3242 |
| | | | | 210/638 |
| 2007/0117222 A1 * | 5/2007 | Sibanda | | G01N 30/14 |
| | | | | 436/518 |
| 2010/0140173 A1 | 6/2010 | Shu et al. | | |
| 2010/0200509 A1 | 8/2010 | Suh et al. | | |
| 2011/0180482 A1 | 7/2011 | Leach et al. | | |
| 2012/0175368 A1 | 7/2012 | Dimson et al. | | |
| 2012/0214974 A1 | 8/2012 | Dawson | | |
| 2013/0330251 A1 | 12/2013 | Tajima | | |
| 2014/0073825 A1 * | 3/2014 | Turlapati | | B01J 35/0013 |
| | | | | 585/240 |

OTHER PUBLICATIONS

International Search Report and Written Opinion, PCT/US2016/025100, dated Jul. 14, 2016.
European Search Report 15795432.2, dated Nov. 14, 2017.

* cited by examiner

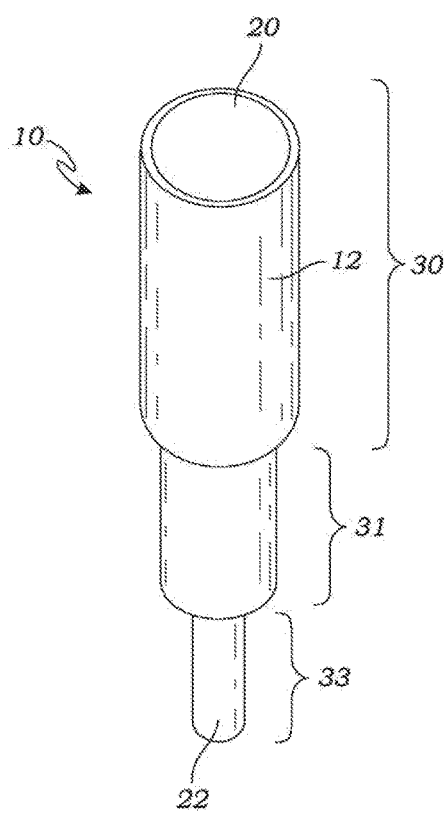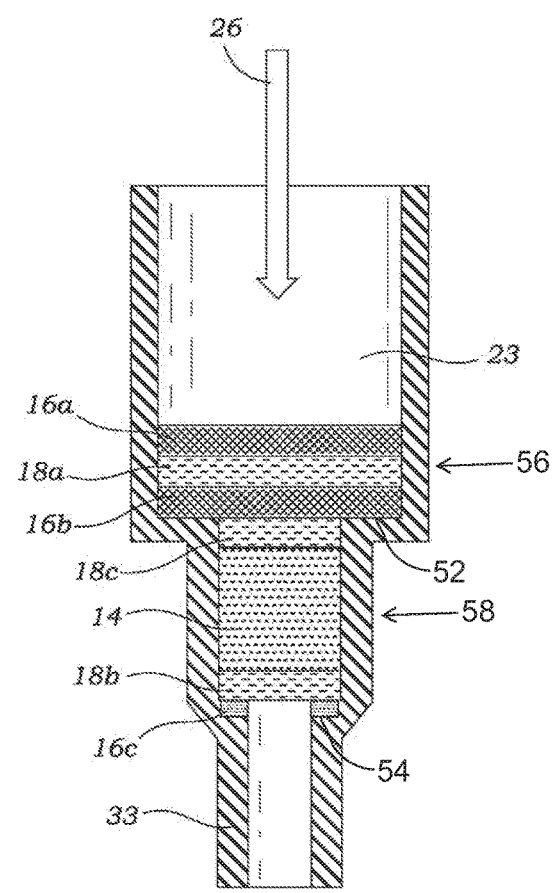
Fig. 1A
Fig. 1B

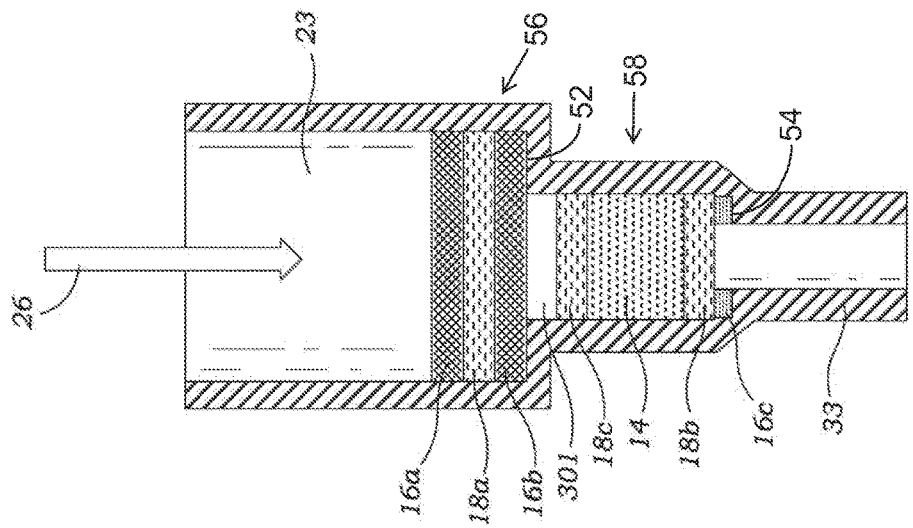
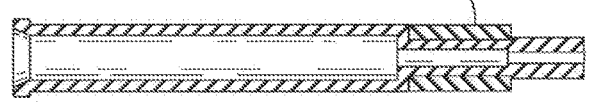
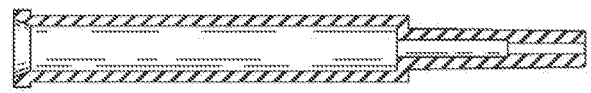
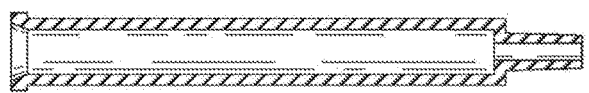

SAMPLE EXTRACTION APPARATUS WITH MICRO ELUTION BED DESIGN

This application claims the benefit of priority pursuant to 35 U.S.C. 119(e) to U.S. Provisional Patent Application 62/000,759, filed on May 20, 2014, the contents of each of which are hereby incorporated by reference in its entirety.

The present invention relates to microcolumns for extraction of an analyte from a liquid sample, and particularly extraction of an analyte from biological fluids.

Accurate and inexpensive detection of analytes present in liquid samples, for example in biological fluids, such as blood and urine, is important to health care. Tests for analytes in blood and urine are conducted to monitor the health of patients, detect the presence of disease conditions, and monitor for the use of illegal or restricted drugs. For example, doctors, when administering drugs such as anti-arrythymics, asthmatic drugs, insulin, and anticoagulants, check the drug content of the blood to regulate the dosages of the patient. Drugs that can be abused, such as heroin, marijuana, cocaine, and codeine, can be tested to determine abuse of the drug, such as by employees and by athletes.

A technique used for detection of analytes includes selectively extracting the analyte from the biological fluid onto a solid media. The analyte is then removed from the solid media by a suitable elution liquid, and tests are conducted to determine whether the analyte is present in the eluent liquid. These tests are conducted using Gas Chromatography-Mass Spectrometry or Liquid Chromatography-Mass Spectrometry.

Extraction columns have been used in the past. For example, particulate silica has been used as the solid media in a column. In addition, media has been sandwiched between frits in a in a column with a single diameter cylindrical shape. Although these prior art devices can be effective, it is desirable to improve on these devices, and their impact in the overall process and their downstream environmental impact. It is desirable that the extraction device improve process throughput, remove a very high percentage of the analyte from the sample, be transportable, storable without damage, and be inexpensive. Moreover, it is desirable that any such device be compatible with existing automated equipment, and not leach into the biological or other fluid samples the eluent liquid or any compound that could interfere with the analytical results. Likewise, it is desirable to minimize the media bed volume and associated dead volumes to lower the volume of the wash eluent liquid. By minimizing the liquid volume, a more concentrated sample is obtained for analysis, the sensitivity of the test is enhanced. High yields from the sample fluid with minimum elution volumes can be obtained by maintaining uniform flow through the extraction media, with no channeling and no dead volume.

SUMMARY

Embodiments of the present invention include an apparatus for extraction of an analyte from a liquid sample. The apparatus includes a container having an entrance, an exit, and a passage therebetween for passage of the liquid sample containing an analyte therethrough, said container having a full diameter bed region and a reduced diameter bed region. The apparatus includes a layered construction having a top and a bottom extending across the passage, comprising from top to bottom: (i) an upper flow distributor/support layer, (ii) an upper compression layer, (iii) an extraction layer of microparticulate extraction medium adjacent to the layer (ii), and (iv) a lower compression layer located adjacent to the extraction layer (iii), where the (i) upper flow distributor and (ii) upper compression layer are located in the full diameter region, the (iii) extraction layer and (iv) lower compression layer are located in the reduced diameter region. In additional embodiments, the apparatus may include a seven layered construction including (i) an upper flow distributor, (ii) an upper compression layer, (i') an middle flow distributor, (ii') a middle compression layer in the reduced diameter region, (iii) an extraction layer of microparticulate extraction medium adjacent to the layer (ii'), (iv) a lower compression layer adjacent to layer (iii), and (v) optionally, a lower flow distributor, wherein layers (i), (ii), (i'), and (ii') are located in the full diameter region, and layers (iii)-(v) may be located in the reduced diameter region.

In one embodiment, the apparatus has one or more air gap layers. In one embodiment an air gap layer is located in the reduced-diameter region. The air gap layer of a further embodiment has a height that ranges from ½ the diameter of the reduced diameter region to 4 times the diameter of the reduced diameter region. In yet a further embodiment, an air gap layer is located between layer (i') and layer (ii'). In still a further embodiment, the air gap layer is located in the reduced diameter region.

The ratio between the effective area of the full diameter region and the reduced diameter region may also vary. The effective area of the full diameter region is $A_F = \pi r_F^2$, where $r_F$ is the radius of an interior surface of the container in the full diameter region, and the effective area of the reduced diameter region is $A_r = \pi r_r^2$ where $r_r$ is the radius of an interior surface of the container in the reduced diameter region. The ratio between the effective bed area of the full diameter region and the effective area of the reduced diameter region ranges from about 10:1 to 1.5:1. In one embodiment the ratio between the effective area of the extraction media to the effective area of the upper compression layer is about 1:10. In a further embodiment the ratio between the effective area of the extraction media to the effective area of the upper compression layer is about 1:4. In another embodiment, the ratio between the effective area of the full diameter region and the effective area of the reduced diameter region is about 4:1.

The extraction media may also be tailored to work with a particular analyte. In one embodiment wherein the extraction media has a number average particle size of about less than 20 μm. In a further embodiment, the extraction media has a number average particle size of about less than 10 μm.

The present apparatus may have a plurality of containers arranged in an array, optionally having a collection plate with a corresponding array of wells.

Further embodiments of the invention are directed to methods of using the present apparatus, and kits including the present apparatus.

The present invention and its multiple embodiments are described further below. Of course, variations on these described embodiments will become apparent to those of ordinary skill in the art upon reading the present description, and thus, one of skill in the art would recognize suitable combinations and variations.

BRIEF DESCRIPTION OF THE SEVERAL VIEWS OF THE DRAWING

FIG. 1A is a perspective view of the exterior of the present apparatus. FIG. 1B is one embodiment of the layers used in the present apparatus.

FIG. 2A is a cross-sectional view of a conventional microcolumn. FIG. 2B is a cross-sectional view of the present apparatus. FIG. 2C provides a vertical cross-section of the present apparatus with one or more ribs 50 on the exterior. FIG. 2D is a horizontal cross-section of the lower narrow diameter portion of the present apparatus, showing the ribs used in a luer tip system. FIG. 2E is an exterior view of the present apparatus including the luer tip at the exit end of the present apparatus.

FIG. 3 is an embodiment of the layers used in the present apparatus which include an air gap.

DETAILED DESCRIPTION

Figure 4A:
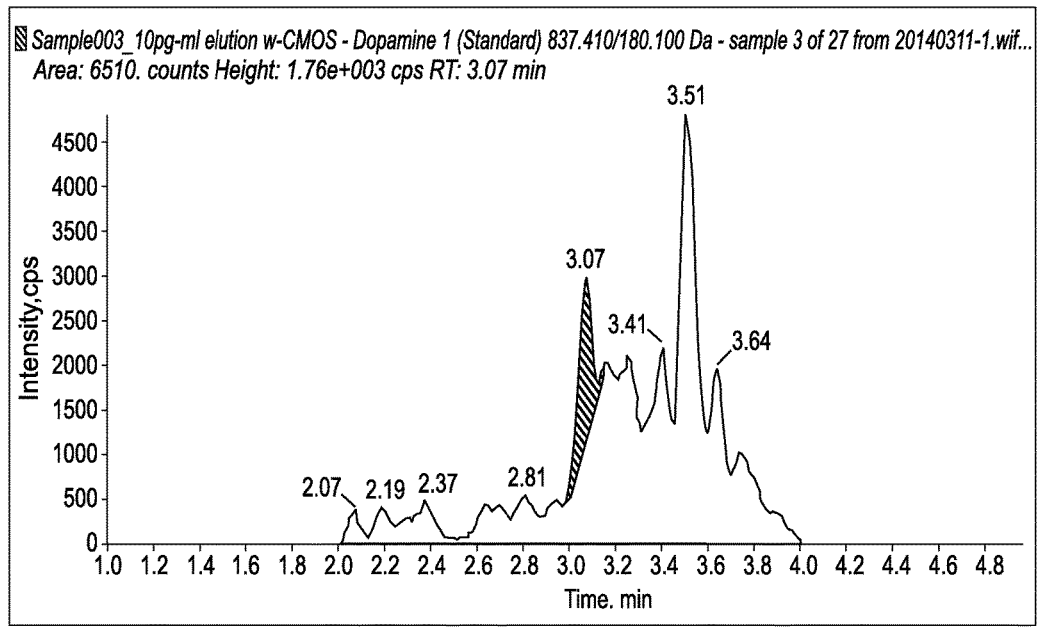
FIG. 4A is exemplary data obtained with the present apparatus using 10 pg/ml of dopamine.
Figure 4B:
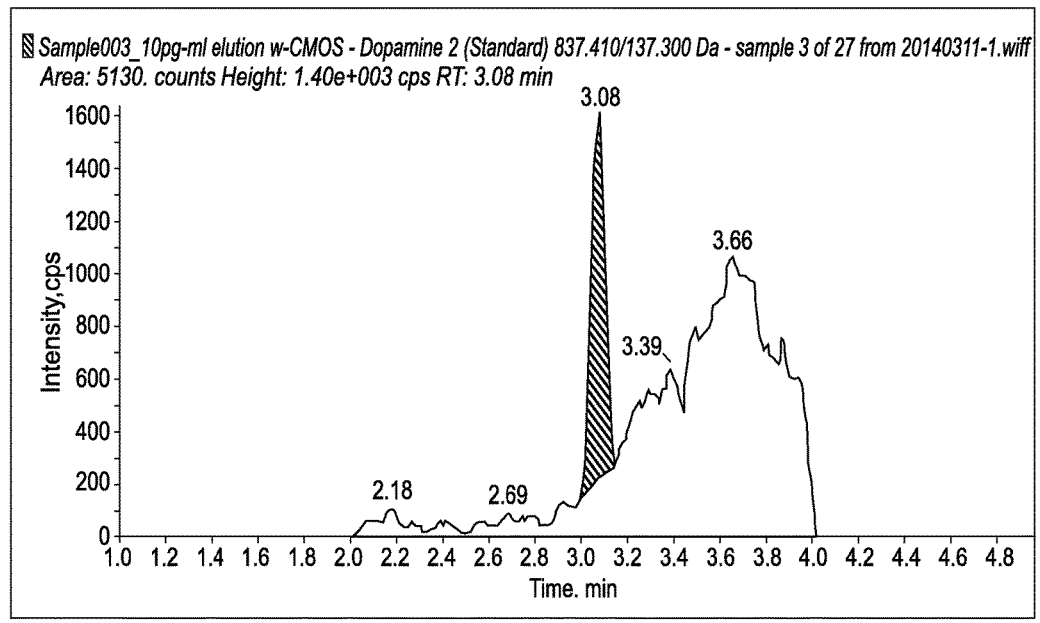
FIG. 4B is exemplary data obtained with the present apparatus using 10 pg/ml of dopamine.
Figure 4C:
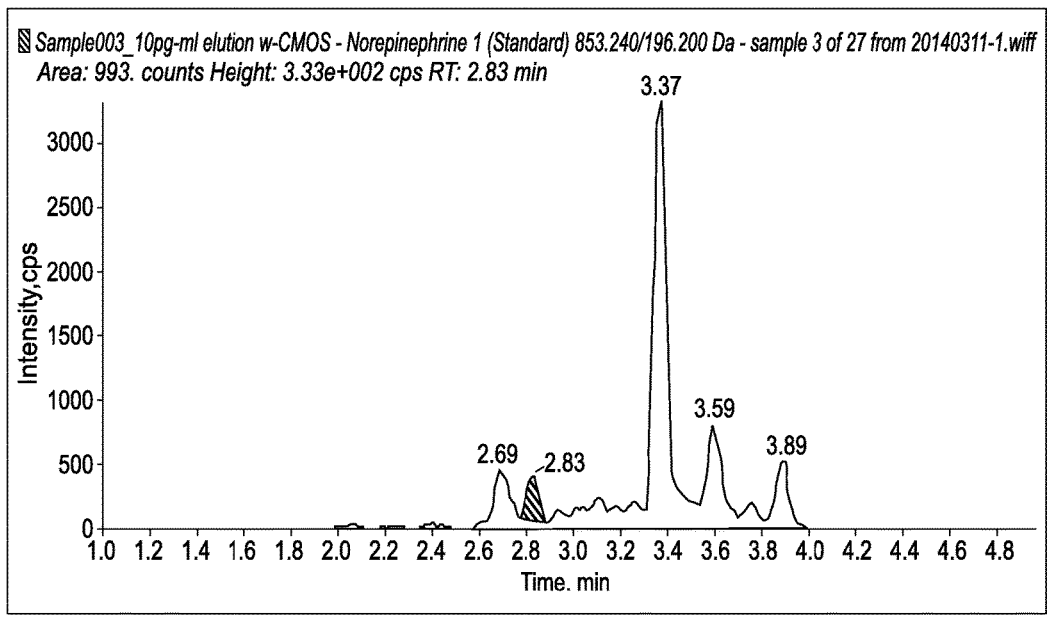
FIG. 4C is exemplary data obtained with the present apparatus using 10 pg/ml of norepinephrine.
Figure 4D:
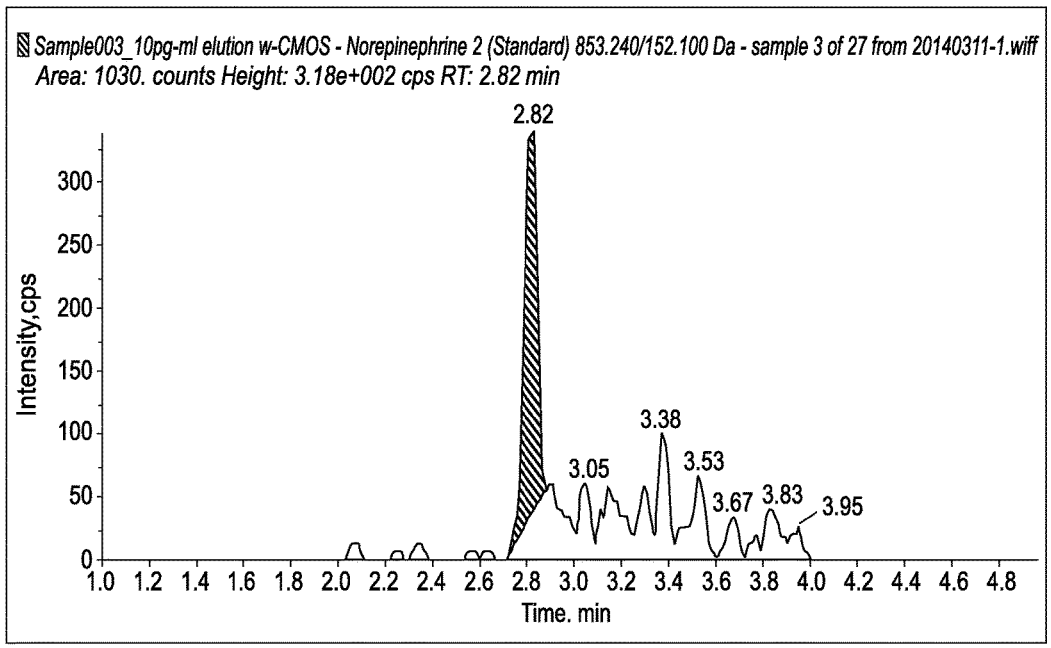
FIG. 4D is exemplary data obtained with the present apparatus using 10 pg/ml of norepinephrine.
Figure 4E:
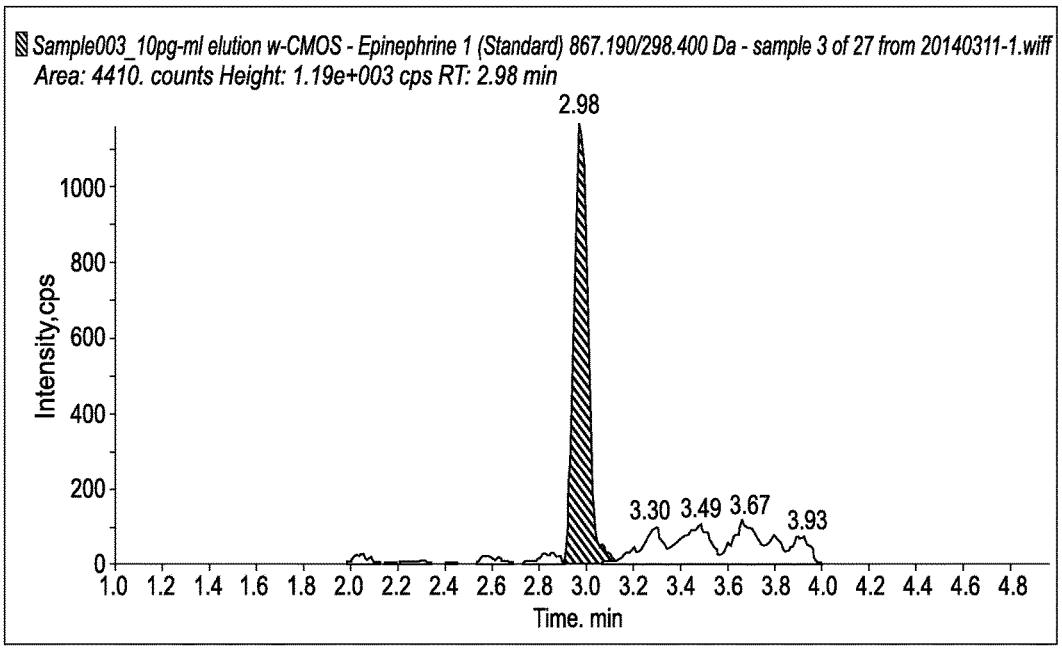
FIG. 4E is exemplary data obtained with the present apparatus using 10 pg/ml of epinephrine.
Figure 4F:
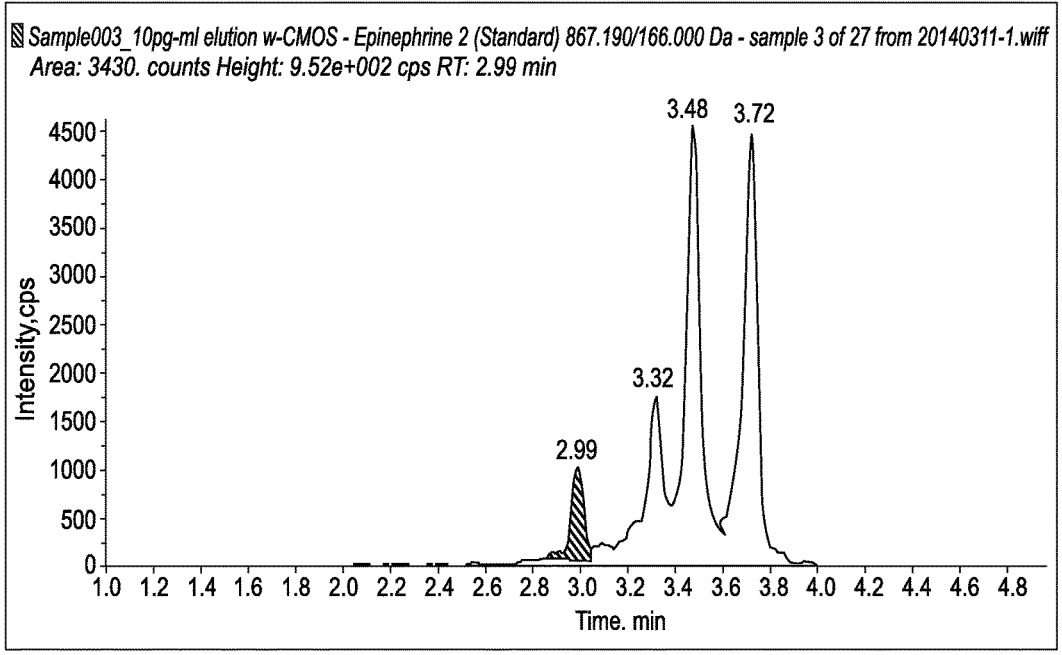
FIG. 4F is exemplary data obtained with the present apparatus using 10 pg/ml of epinephrine.
Figure 5A:
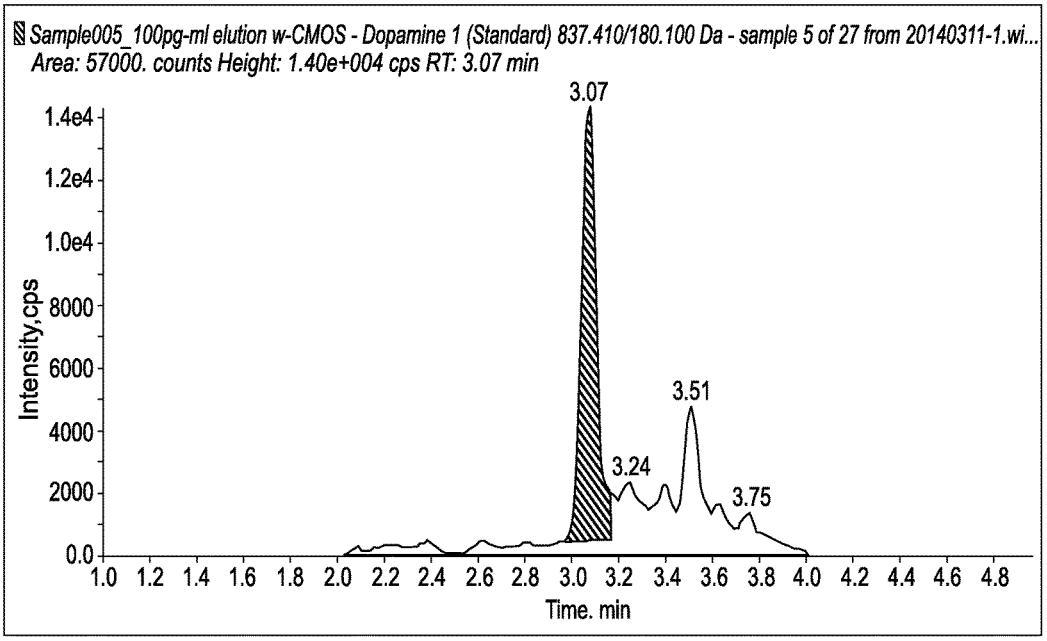
FIG. 5A is exemplary data obtained with the present apparatus using 100 pg/ml dopamine.
Figure 5B:
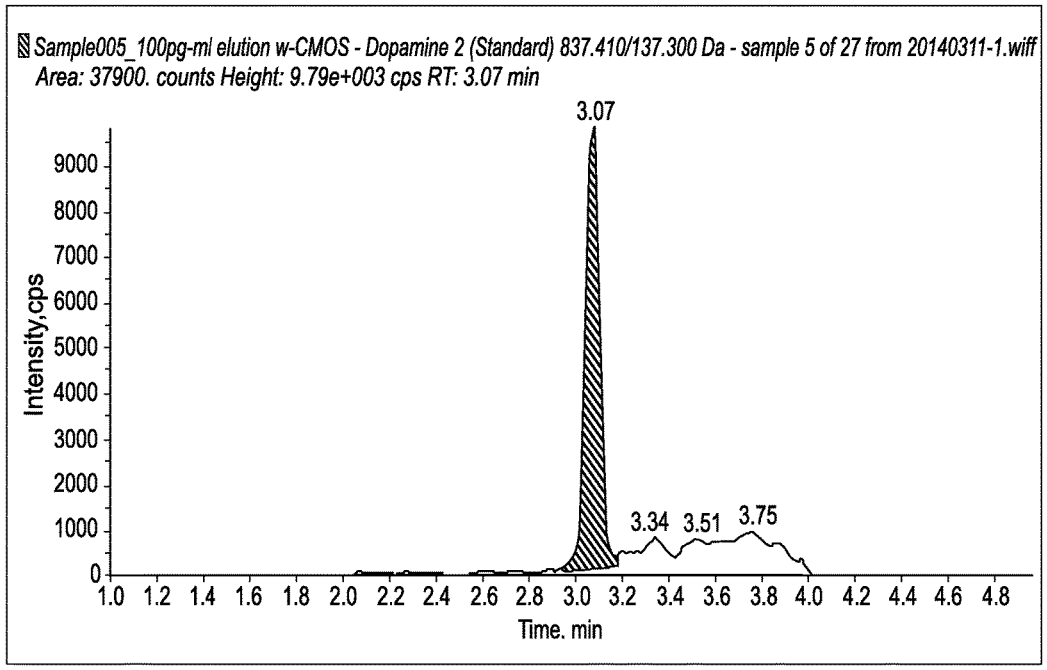
FIG. 5B is exemplary data obtained with the present apparatus using 100 pg/ml of dopamine.
Figure 5C:
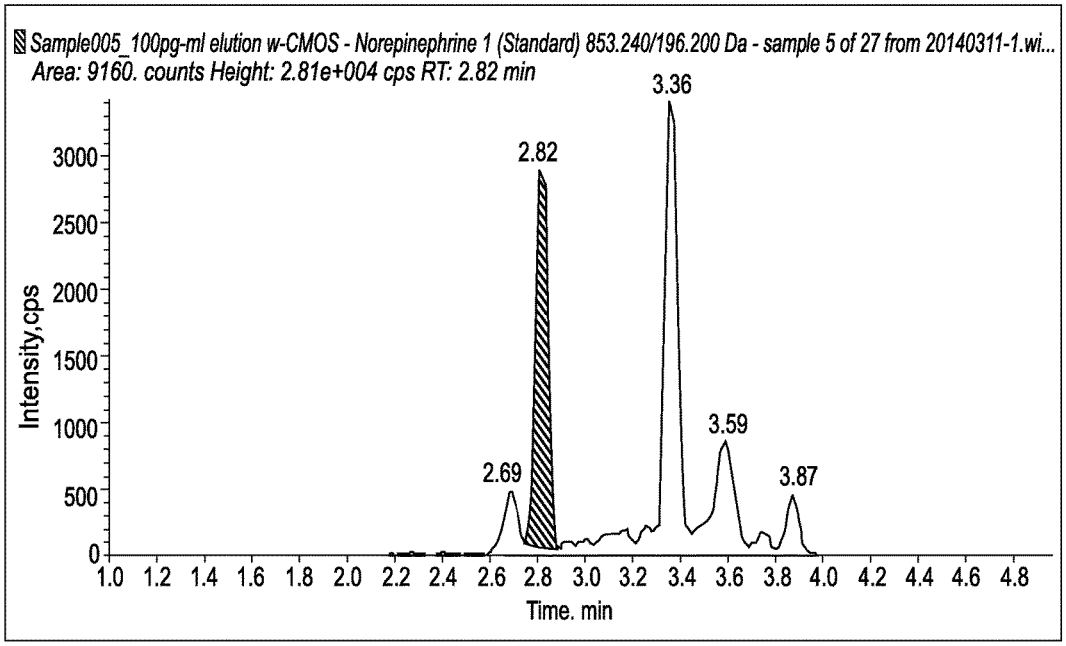
FIG. 5C is exemplary data obtained with the present apparatus using 100 pg/ml of norepinephrine.
Figure 5D:
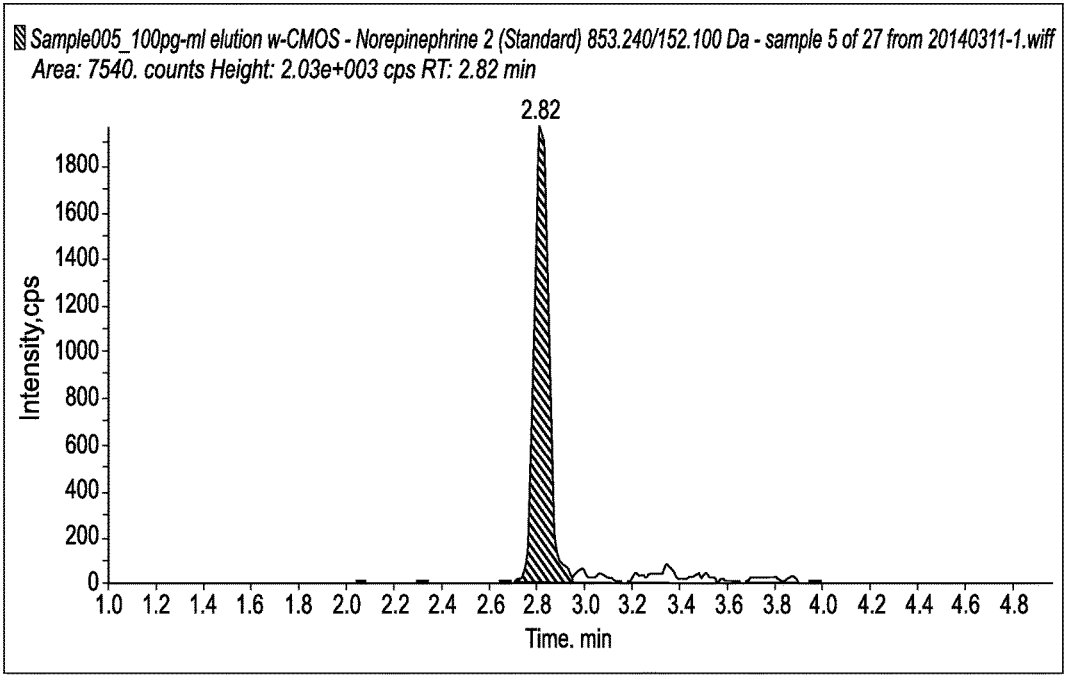
FIG. 5D is exemplary data obtained with the present apparatus using 100 pg/ml of norepinephrine.
Figure 5E:
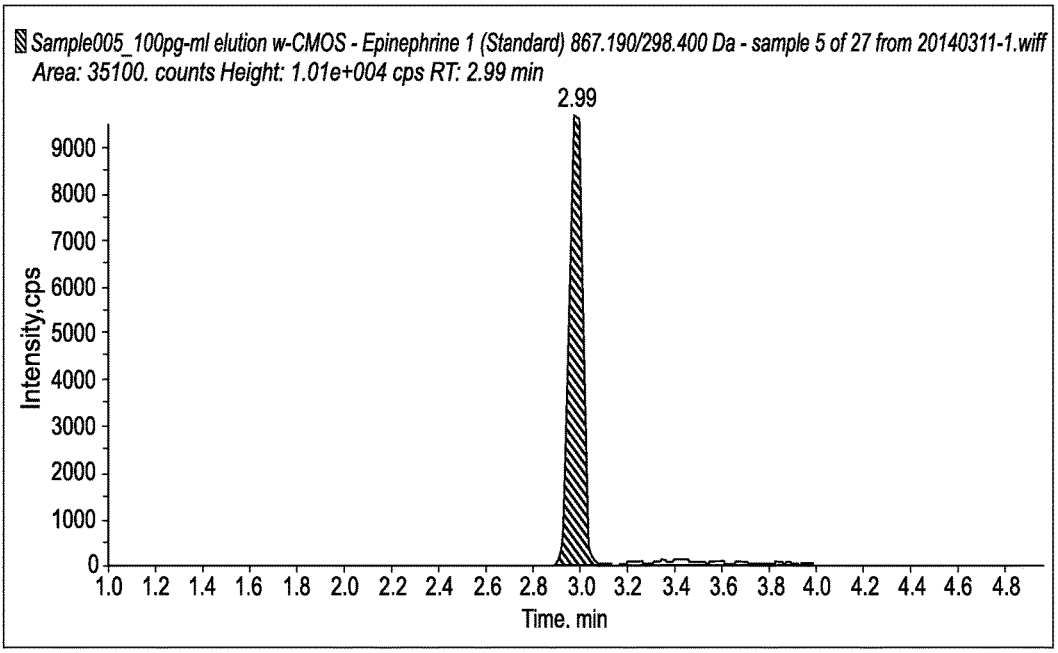
FIG. 5E is exemplary data obtained with the present apparatus using 100 pg/ml of epinephrine.
Figure 5F:
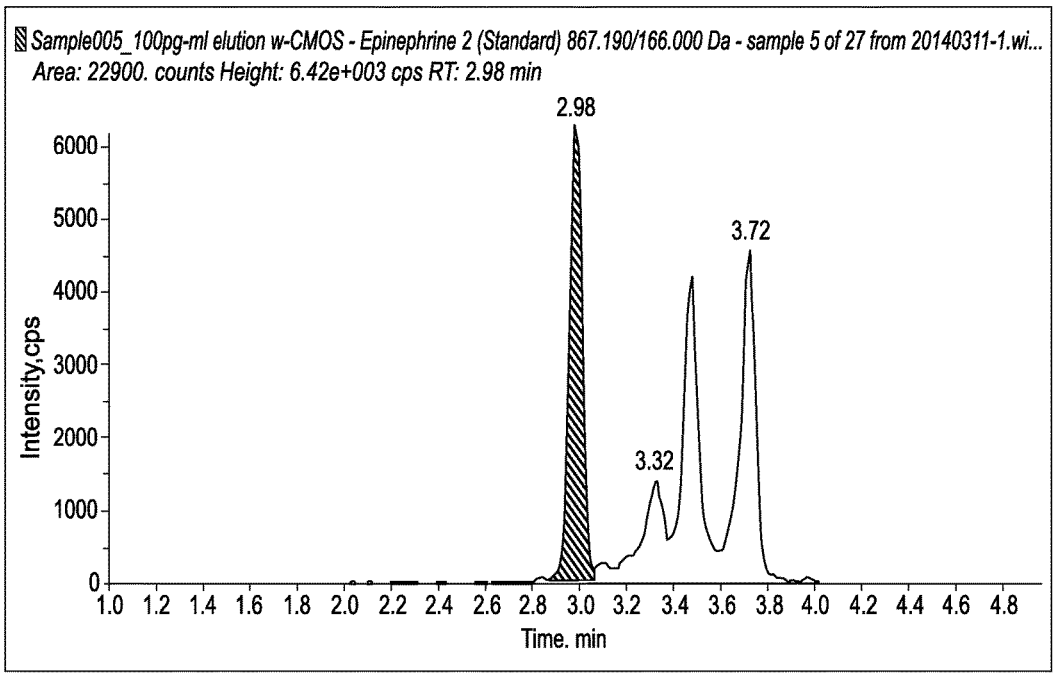
FIG. 5F is exemplary data obtained with the present apparatus using 100 pg/ml of epinephrine.

The present invention is directed to an extraction apparatus that meets the needs of: improving downstream environmental impact and process throughput, removing a very high percentage of the analyte from the sample, transportability, storage without damage, price point, compatibility with existing automated equipment, leaching characteristics, minimization of the media bed volume and associated dead volumes, enhancing sensitivity and uniformity of flow through the extraction media.

The present apparatus is useful for extracting an analyte from a liquid sample and comprises a container, typically a microcolumn, having an entrance, an opposed exit, and a passage there between for passage of a liquid sample containing an analyte therethrough.

The microcolumn of the present apparatus has at least two regions in the passage of the analyte: an area having a full diameter bed (aka the "full diameter region", shown in FIG. 1 as 30) and an area having a reduced diameter bed (aka the "reduced diameter region", shown in FIG. 1 as 31). As used herein, "diameter bed area" is measured by the surface area of a horizontal cross-section of the interior cavity of the container. Therefore, for a cylindrical container the diameter bed is the area of the circle ($\pi r^2$) whose diameter ($=2r$) extends from one side of the interior cavity of the container to the other side of the interior cavity. The diameter bed may also be referred to as the "effective area" of a particular layer.

Within the passage in the region of reduced diameter bed 31 is a layer of a microparticulate extraction media. Extraction media 14 may include any known sorbent and a variety of particles. The sorbent particles employed in the apparatus include any particulate matter that is capable of having at least one substance, either target or interfering, adhered thereto. Illustrative examples of sorbent particles that may be employed in the present invention include, but are not limited to: ion exchange sorbents, reversed phase sorbents, and normal phase sorbents. More particularly, the sorbent particles may be an inorganic material such as $SiO_2$ or an organic polymeric material such as poly(divinylbenzene). In some embodiments of the present invention, the sorbent particles may be treated with an organic functional group such as a $C_2$-$C_{22}$, preferably $C_8$-$C_{18}$ functional group. In one embodiment, the sorbent of the extraction media includes silica based particles (such as silica based carboxylic acids), diatomaceous earth particles, polymeric based particles, mono-dispersed silica and polymeric particles, and/or carbon graphite particles. The media is selected for extracting the analyte from the liquid sample. A suitable silica extraction media is described in U.S. Pat. No. 4,650,714, which is incorporated herein by reference. A preferred microparticulate silica extraction media is available from Avantor Performance Materials (previously known as J.T. Baker Chemical Company) of Phillipsburg, N.J., and is sold under their catalog number 7049-01.

The extraction media has a small particle size having a number average particle size of less than about 40 microns, less than about 30 microns, less than about 25 microns, less than about 20 microns, less than about 15 microns, less than about 10 microns, or less than about 5 microns. In one embodiment, the extraction media has a number average particle size of less than about 20 microns, or more preferably less than about 10 microns. In addition, the extraction media does not have to be homogenous, but rather a different extraction media can be used in a single bed, or the apparatus can include multiple beds of extraction media for extracting different analytes from samples.

The extraction media is sandwiched between at least two compression layers. In one embodiment, the diameter bed area of the extraction media is lower than the diameter bed area of the upper compression layer, such that the ratio of the effective area of the upper compression layer to the effective area of the extraction media layer is about 10 to 1, about 9 to 1, about 8 to 1 about 7 to 1 about 6 to 1, about 5 to 1, about 4 to 1, about 3 to 1, about 2 to 1, or about 1.5 to 1. In one embodiment, the ratio of the effective area of the upper compression layer to the effective area of the extraction media layer is about 4 to 1.

The extraction media may be loosely packed (where the sorbent is loosely sandwiched between the compression layers and free to move) or a compacted extraction media bed (where the extraction media is compacted between the two layers, or has relatively little additional possible space between particles).

The extraction media is sandwiched between either the upper compression layer 18a and lower 18b compression layer or middle compression layer 18c and lower 18b compression layer, and compress the extraction media there between. Upper compression layer 18a is located in full diameter region 30, middle compression layer 18c may be located in either the full diameter region 30 or reduced diameter region 31, and lower compression layer 18b is located in reduced diameter region 31. In one embodiment only two compression layers are used. In one embodiment, at least three compression layers are used.

The compression layers are sufficiently porous that the liquid sample can flow therethrough, and are formed from a flexible material. One or more of the compression layers may be flat, spherical, or optimally shaped to suit the fluid flow through the apparatus (such as a truncated cone, prismatic, truncated pyramid etc.). FIG. 3 shows an embodiment where middle and lower compression layers (18c and 18b respectively) are spherical. A mixture of shapes of compression layers may be used in a single microcolumn.

The narrow bore sandwich design pairs with the low dead volume column design for function. The chief purpose of compression layers 18 is to hold the extraction media in place and compressed as a thin extraction layer. In one embodiment, one or more of the compression layer(s) has a pore size less than the particle size of the extraction media and functions as a flow rate limiter. They are sufficiently porous that the liquid sample can flow therethrough, and are composed of a flexible, hydrophilic material. The compression layer is preferably formed of a spongy, glass fiber, having no binder.

A suitable compression layer comprises a glass microfiber media made of analytically clean material. Suitable materials, which are available from Whatman Specialty Products, Inc. of Fairfield, N.J., include borosilicate glass fibers that are analytically clean and include no binder. This material, when purchased, has a smooth side and a rough side, where the smooth side is of lower porosity than the rough side. Preferably, it is the smooth side that is placed in contact with the microparticles of extraction layer 14. Other suitable materials include frits and filters; such as polymer (e.g., polypropylene or polyethylene) frit materials. Said frits or filters may be cylindrical, die cut, or spherical, having a diameter to fit the interior cavity of the column; for instance, in the full diameter portion or in the reduced diameter portion.

Preferably compression layers 18 are resilient or "spongy" to hold the microparticles in place. In one aspect, the pore size for the compression layers is less than 10 microns, less than 5 microns, or less than 3 microns. Compression layers 18 generally are of the same thickness, having a thickness typically of from about 0.1 mm to about 3.25 mm, about 0.25 mm to about 3.25 mm, about 0.5 mm to about 3.0 mm, about 0.75 mm to about 3 mm, about 0.25 mm to about 2.5 mm, about 0.25 mm to about 2 mm, about 0.25 mm to about 1.5 mm, about 0.25 mm to about 1.25 mm, about 0.25 mm to about 1.0 mm, about 0.1 mm to about 0.75 mm, or about 0.1 mm to about 0.5 mm. In one aspect the compression layer(s) have a thickness of about 0.5 mm.

This is in contrast to the prior art microelution columns, which are made with cylindrical syringe barrel tubes, or funnel shaped sample reservoirs (see e.g., US 2006/0163163). Although some of these microelution columns have reduced dead volume after the bed, these designs do not address the ratio between the effective area of the upper compression layer compared to the effective area of the extraction media layer.

Reducing the effective area ($\pi r^2$) of the extraction media bed about 4-1 in relation to the effective area of the upper compression layer, leads to a corresponding reduced volume of sorbent material and reduced dead volumes for the reagent.

Flow distributors 16, which are formed of a flexible mesh material, help provide uniform flow of the sample through the column, and physically retain the compression layers and microparticulate material in place in the column. Preferably, the mesh is 200 mesh or smaller, (i.e., has a mesh number of 200 or higher). In aspects of this embodiment, the mesh number is 150 or higher, 170 or higher, 200 or higher, 250 or higher, 270 or higher, 325 or higher, or 400 or higher.

The mesh may be made of any flexible bio-inert material. It one embodiment it is made of Polyphenelyne Sulfide (PPS), Polytetrafluoroethylene (PTFE), Polyether ether Ketone (PEEK), Polyoxymethylene (POM), Ethylene Propylene Diene (EPDM), a Fluorinated elastomer (FKM), a Perfluoro elastomer (FFKM), polysulfone (PSU), Ethylene Tetrafluoroethylene (ETFE), Polypropylene (PP), (Poly)Chlorotrifluoroethylene (PCTFE/CTFE), polystyrene, high density polyethylene, polycarbonate, nylon, polyethylene terephthalate (PET), silicon, rubber, or polyester. In aspects of this embodiment it is made of polypropylene, or alternatively, polytetrafluoroethylene. A suitable material is available from Tetko, Inc. of Briarcliff Manor, N.Y., under catalog number 5-420134.

In one embodiment the microcolumn also includes an upper mesh flow distributor above the upper compression layer for support, and, optionally, a middle flow distributor and/or a lower flow distributor. In one embodiment, the flow distributors may be layered or molded, in the housing above and below the compression layer(s), sandwiching the compression layers and the layer of extraction media therebetween. The flow distributors hold the extraction media and the compression layers in the microcolumn and help distribute flow of the liquid sample to avoid channeling. As shown in the embodiment of FIG. 1B, the upper flow distributor 16a is located in the full diameter region, the middle flow distributor 16b is also located in the full-diameter region and the lower flow distributor 16c, if used, seats in the lower portion of the column, having a reduced diameter. In one embodiment, the upper flow distributor 16a is sized so that it is held in the bore of microcolumn 12 by a compression fit. Similarly, the other flow distributor layer(s) may also be sized for a compression fit. A first shelf 52 is defined within the passage between the full diameter bed region 30 and the reduced diameter bed region 31; and a second shelf 54 is defined within the passage 23 between the reduced diameter bed region 31 and the tip region 33. A first media assembly 56 is positioned within the passage 23 in the full diameter bed region 30 and is positioned atop, seated on, and contacting the first shelf 52; and a second media assembly 58 is positioned within the passage 23 in the reduced diameter bed region 31 atop, seated on, and contacting the second shelf 54. In an exemplary embodiment the second media assembly 58 can include at least an extraction media 14 with sorbent properties, and may further include compression layers 18b, 18c and a flow distributor 16c. In an exemplary embodiment the first media assembly can include at least one of an upper flow distributor 16a, a middle flow distributor 16b, and an upper compression layer 18a.

Due to the combination of the narrow bore extraction media and the compression layer sandwich, rapid extraction of an analyte from a fluid can be obtained, with the apparatus being configured for very small volumes of elution liquid on the order of about 0.025 mL to about 0.25 mL, about 0.025 mL to about 0.2 mL, about 0.025 mL to about 0.15 mL, about 0.025 mL to about 0.100 mL, down from 0.5 mL to 1.5 mL. This smaller elution volume fits directly into autosampler trays for automation. Smaller volumes eliminate concentration steps and vial transfers and associated cross contamination fails. In addition, the extraction device of the present invention is inexpensive to use and manufacture, is stable during storage and transportation, and is compatible with existing automated equipment. The experimental data below displays the effective improvement in performance of a clinical assay done using regular Cerex columns versus the Narrow Bore version (the presently disclosed columns).

An apparatus for extracting an analyte from a liquid sample is shown in FIG. 1A. As shown in FIG. 1A, the apparatus comprises microcolumn 12, which serves as a container for an extraction sandwich system. In one embodiment, microcolumn 12 has generally a tubular configuration, and has entrance 20, opposed exit 22, and passage 23 therebetween. Passage 23, which is also referred to as a central bore, contains the extraction system. Passage 23 has two regions, upper full diameter bed region 30 and lower, reduced diameter bed region 31. The exit 22 may optionally be located in a separate region, with a "tip" configuration.

The various layers may be located adjacent to each other, and may or may not be in direct contact with the surrounding layers. That is, there may be one or more Air Gaps (FIG. 3, 301) between two layers which are deliberately located to prevent dripping or capillary flow and allow for the transfer of the column to an appropriate receiving vessel or plate. For instance, in one embodiment, there is an Air Gap layer (FIG. 3, 301) between the middle flow distributor (FIG. 3, 16b) and the middle compression layer (FIG. 3, 18c). That is, in one embodiment, there may be an air gap between the layers that straddle the transition from full-diameter region to reduced diameter region. In another embodiment there may be a strategic Air Gap 301 located after the lower compression layer (FIG. 3, 18b) but before the lower distributor layer (optionally shown in FIG. 3 as 16c).

In one embodiment, the Air Gap is positioned at or below the top edge of the reduced diameter region, and may have a height ranging from ½ of the diameter of the reduced diameter region to 4 times the diameter of the reduced diameter region. In aspects of this embodiment, the height of the air gap may be from, e.g., about ½ to about 1 times, about ½ to about 1.5 times, about ½ to about 2 times, about ½ to about 2.5 times, about ½ to about 3 times, about ½ to about 3.5 times, about ½ to about 4 times, about 1 to about 1.5 times, about 1 to about 2 times, about 1 to about 2.5 times, about 1 to about 3 times, about 1 to about 3.5 times, about 1 to about 4 times, about 1.5 to about 2 times, about 1.5 to about 2.5 times, about 1.5 to about 3 times, about 1.5 to about 3.5 times, about 1.5 to about 4 times, about 2 to about 2.5 times, about 2 to about 3 times, about 2 to about 3.5 times, about 2 to about 4 times, about 2.5 to about 3 times, about 2.5 to about 3.5 times, about 2.5 to about 4 times, about 3 to about 3.5 times, about 3 to about 4 times, or about 3.5 to about 4 times, the diameter of the reduced diameter region.

When placed strategically at the inlet to the reduced diameter region, the air gap prevents the unassisted capillary flow of certain classes of solvents or samples from bridging the gap for capillary transfer down to the next layer and then through the media bed. The air gap is particularly useful in areas with smaller diameters because the strength of the air gap is based on the surface tension between the liquid flowing through the apparatus and the gas located in the air gap.

The gap height may vary by the intended analytes to be tested, and might not be there at all. The Air Gap is particularly useful in a method where the compression layers are wet or preconditioned before the test sample is added to the microcolumn.

The structure of tip region 33 is not particularly limited and in one embodiment may be cylindrical or conical. Tip region 33 may have the same diameter bed as the reduced diameter bed region, a smaller diameter bed than the reduced diameter bed region. In one embodiment, the tip region 33 has the same footprint as the reduced diameter bed region, in another embodiment, the footprint of the tip region has a differently shaped footprint than the reduced diameter bed region. In one embodiment, tip region 33 is optionally in the form of a luer tip or similar, which allows apparatus 10 to be used with conventional automated extraction apparatus, which are designed to receive an extraction column having a luer tip. FIG. 2C provides a vertical cross-section of the present apparatus with one or more ribs 50 on the exterior. FIG. 2D is a horizontal cross-section of the lower narrow diameter portion of the present apparatus, showing the ribs used in a luer tip system. FIG. 2E is an exterior view of the present apparatus including the luer tip system at the exit end of the present apparatus.

A liquid sample flows in the direction of arrow 26 shown in FIG. 1B through the passage 23.

The portion of microcolumn 12 above the extraction sandwich system serves as a reservoir for the liquid sample, from which an analyte is to be extracted, and also a reservoir for an eluent liquid.

In one embodiment, the extraction system includes a four layer sandwich construction with: (i) an upper flow distributor/support, (ii) an upper compression layer, (iii) an extraction layer, and (iv) a lower compression layer, where the upper flow distributor is located in the full diameter region and upper compression layer, the extraction layer and lower compression layer are located in the reduced diameter region.

In one embodiment, the extraction system is comprised of a six layer sandwich construction, including (i) an upper flow distributor, (ii) a cylindrical or fabric compression layer, a (ii) lower flow distributor, (iv) a spherical frit as a compression layer, (v) the microparticulate extraction medium, and (vi) a spherical frit as a lower compression layer. Layers (i)-(iii) would reside in the full-diameter region, where layers (iv)-(vi) would reside in the reduced diameter region.

In one embodiment (shown in FIG. 1B), the extraction system is comprised of a seven-layer sandwich construction, that includes (i) upper flow distributor 16a, (ii) upper compression layer 18a (iii) middle flow distributor 16b, (iv) middle compression layer in the reduced diameter region 18c, (v) extraction layer 14 of microparticulate extraction medium, (vi) lower compression layer 18b, (vii) and optionally, lower flow distributor/support 16c which may be molded as part of the container. In this embodiment, layers (i)-(iii) may be located in the full diameter region, and layers (iv)-(vii) may be located in the reduced diameter region. Alternatively, the division between full diameter and reduced diameter may occur between layers (ii) and (iii). Additional layers may be added.

In a further embodiment (shown in FIG. 3), the extraction system is comprised of an eight-layer sandwich construction, that includes: (i) upper flow distributor 16a, (ii) upper compression layer 18a (iii) middle flow distributor 16b, (iv) air gap layer 301, (v) middle compression layer in the reduced diameter region 18c, (vi) extraction layer 14 of microparticulate extraction medium, (vii) lower compression layer 18b, (viii) and optionally, lower flow distributor/support 16c which may be molded as part of the container. In this embodiment, layers (i)-(iii) may be located in the full diameter region, and layers (iv)-(viii) may be located in the reduced diameter region. Alternatively, the division between full diameter and reduced diameter may occur between layers (ii) and (iii). Additional layers may be added.

All of the components of apparatus 10 are made of materials that are substantially inert to biological fluids so that when a biological fluid such as blood or urine is passed through apparatus 10, substantially nothing passes from apparatus 10 into the blood or urine. In one embodiment, microcolumn 12 is made of a biologically inert material. In one aspect, the biologically inert material is a plastic. In aspects of this embodiment, the biologically inert material is a fluorinated polymer or polypropylene. In other aspects the material is Polyphenelyne Sulfide (PPS), Polytetrafluoroethylene (PTFE), Polyether ether Ketone (PEEK), Polyoxymethylene (POM), Ethylene Propylene Diene (EPDM), a Fluorinated elastomer (FKM), a Perfluoro elastomer (FFKM), polysulfone (PSU), Ethylene Tetrafluoroethylene (ETFE), Polypropylene (PP), (Poly)Chlorotrifluoroethylene (PCTFE/CTFE), polystyrene, high density polyethylene, polycarbonate, nylon, or polyethylene terephthalate (PET), silicon, rubber, polyester, or ceramics.

A typical microcolumn according to the present invention has an internal diameter of about 0.01 inch to about 2 inches, about 0.025 inches to about 1.75 inches, about 0.05 inches to about 1.5 inches, of about 0.075 inches to about 1.25 inches, of about 0.1 inches to about 1 inch. In other aspects of this embodiment, the internal diameter is at least 0.01 inch, at least 0.025 inches, at least 0.05 inches, 0.075 inches, at least 0.1 inch, at least 0.25 inches, at least 0.5 inches, at least 0.75 inches, at least 1 inch, at least 1.25 inches, at least 1.5 inches, at least 1.75 inches, or at least 2 inches. In still other aspects of this embodiment, the internal diameter is at most 0.01 inch, at most 0.025 inches, at most 0.05 inches, 0.075 inches, at most 0.1 inch, at most 0.25 inches, at most 0.5 inches, at most 0.75 inches, at most 1 inch, at most 1.25 inches, at most 1.5 inches, at most 1.75 inches, or at most 2 inches. In a preferred embodiment the microcolumn has an internal diameter of about 0.1 inch to 1.0 inch.

A typical microcolumn according to the present invention has a length, excluding the tip if present, of about 0.25 inches to about 5 inches, 0.5 inches to about 4.5 inches, 0.5 inches to about 4 inches, 0.5 inches to about 3.5 inches, about 0.5 inches to about 3 inches, about 0.5 inches to about 2.5 inches, about 0.5 inches to about 2 inches, about 0.5 inches to about 1.5 inches, about 0.5 inches to about 1 inch, about 1.75 inches to about 3 inches, about 2 inches to about 3 inches, about 2.5 inches to about 3 inches. In other aspects of the invention, the microcolumn has a length of at least 0.25 inches, at least 0.5 inches, at least 0.75 inches, at least 1 inch, at least 1.25 inches, at least 1.5 inches, at least 2 inches, at least 2.25 inches, at least 2.5 inches, at least 2.75 inches, at least 3 inches, at least 3.25 inches, at least 3.5 inches, at least 3.75 inches, at least 4 inches, at least 4.25 inches, at least 4.5 inches, at least 4.75 inches, or at least 5 inches. In still further aspects, the microcolumn has a length, excluding the tip if present of at most 0.25 inches, at most 0.5 inches, at most 0.75 inches, at most 1 inch, at most 1.25 inches, at most 1.5 inches, at most 2 inches, at most 2.25 inches, at most 2.5 inches, at most 2.75 inches, at most 3 inches, at most 3.25 inches, at most 3.5 inches, at most 3.75 inches, at most 4 inches, at most 4.25 inches, at most 4.5 inches, at most 4.75 inches, or at most 5 inches. In a preferred embodiment, the microcolumn has a length, excluding the tip of about 0.5 inches to about 3 inches. The length of the tip (if present) is not particularly limited but may range from about 0.1 inch to 1 inch.

The upper full diameter region generally includes at least about 40%, 45%, 50%, 55%, 60%, 65%, 70%, 75%, 80%, or 85% of the total microcolumn length. In one embodiment, the upper full diameter region includes at least about 75% of the total microcolumn length.

The microcolumn of the apparatus need not have the shape shown in the figures. For example, it need not be cylindrical, and may instead have a square footprint, a polygonal footprint (e.g., hexagonal, octagonal etc.), tubular, or include combinations of multiple shapes. As used herein "footprint" describes the shape of a horizontal cross-section of the interior cavity (i.e., passage 23) of the microcolumn. In one embodiment, the full diameter bed region has a first footprint shape, and the reduced diameter bed region has a second footprint shape, and the tip (if present) may have a third footprint shape (or may have the same footprint shape as either the full diameter bed region or the reduced diameter bed region).

In addition, in one embodiment of the invention, entrance 20 can be designed or configured to receive a connective fitting to connect the microcolumn to a fluid input device. Such connective fittings include luer tips, luer-lock extensions or tapers of various types, male and female-type connections of various types, threaded connections, or barb connections.

As used herein, a "fluid input device" is any device which is in contact with the entrance and directly transfers the sample or reagent to entrance 20 in a connected manner. Fluid input devices may include automated fluid dispensing systems, automated liquid handling platforms, syringes, and microdispensers. The fluid input device may dispense the sample or reagent to the microcolumn automatically, semi-automatically, or manually. For instance a fluid input device may include a reservoir containing a liquid sample, which once connected to the entrance, can automatically dispense sample to the microcolumn.

The narrow bore sandwich layer in the reduced diameter region can be assembled in as a stand-alone column barrel design or patterned in a one-piece block format for automated processing.

The present apparatus may be in a single column format, which is convenient and cost effective for preparing a small number of samples, or a multi-column array or format (aka, an "extraction plate"), which is suited for preparing large numbers of samples in parallel.

One embodiment of the invention is an extraction plate the narrow bore columns discussed above. This extraction plate may be a molded plate containing a plurality of columns. The columns may be arrayed to align or intercalate with the wells of conventional "multi-well" formats, such that each column would elute into a well in a standard (or custom) multi-well plate. Multi-well formats are commonly used with robotic fluid dispensing systems, such as autosamplers. Typical multi-well formats are not limited, but include 48-, 96-, and 384- and 1,584-well standard plate formats.

Fluids are usually forced through the present apparatus and into the collection containers (or the wells of a "collection tray" or "plate"), either by drawing a vacuum across the device with a specially designed vacuum manifold, or by using centrifugal or gravitational force. In specially designed vacuum manifold systems, the both the column and the receiving means (such as a well or collection tube) may be integrated into the vacuum system to optimize extraction. Centrifugal force is generated by placing the apparatus, together with a suitable collection tube or tray, into a centrifuge specifically designed for the intended purpose. However, in one embodiment gravity may be sufficient to force the fluid through the present apparatus as well.

The present apparatus may use conventional collection containers or collection plates, such as glass tubes, centrifuge tubes, Eppendorf tubes, or standard multi-well plates or trays. The present apparatus may alternately use collection containers specifically designed to be compatible with the present extraction plate.

Methods of using the present invention include extraction of an analyte from a test sample. A test sample refers to any sample that may contain an analyte of interest. A test sample may be a biological sample, that is, a sample obtained from any biological source, such as an animal, a plant, a fungus, a microorganism, a cell culture, an organ culture, etc. In aspects of this embodiment, a biological sample includes a blood sample including a whole blood sample, a plasma sample, or a serum sample, a saliva sample, a urine sample, cerebrospinal fluid sample, a bile sample, a tissue sample, or any other sample that can be obtained, extracted or isolated from a biological source. Such biological samples may be obtained, for example, from a patient; that is, a living person, male or female, presenting oneself in a clinical setting for diagnosis, prognosis, or treatment of a disease or condition. In one embodiment, the sample is obtained from a patient, for example, a plasma specimen. The plasma specimen may be taken with or without the use of anticoagulants.

A test sample may be an environmental sample. Environmental samples are samples taken from dirt, plant matter, or fluid sources (such as ground water, oceans, or rivers etc.). Dirt (aka "soil samples") may be taken from agricultural sites or sites of environmental interest and may have the analyte extracted, including the removal of particulate matter.

The methods of using the present apparatuses include contacting the apparatus with the sample in a liquid buffer, and eluting the sample from the apparatus with an elution buffer. Further steps might include conditioning the apparatus, washing steps (before, during, or after contacting the apparatus with a sample).

The present apparatus may also be included in a kit specifically designed to capture and separate a particular analyte of interest. The microparticulate extraction media may be specifically adapted to separate specific analytes of interest. The kit may include suitable reagents (labels, washes, etc.), buffers or elution buffers, in concentrated form or in a form suitable for direct use. The kit may also include an extraction plate or array of columns as described above, and accompanying couplings to connect the plate to fluid dispensing devices and/or plates or vials for receiving the eluted solution containing the sample.

Although the present invention has been described in considerable detail with reference to certain preferred versions thereof, other versions are possible. For example, the apparatus 10 is not limited to use with biological fluids, but can be used, for example, for testing ground water, drinking water, and other liquids for contaminants.

Aspects of the present specification may also be described as follows:
1. An apparatus for extracting an analyte from a liquid sample comprising: a) a container having an entrance, an exit, and a passage therebetween for passage of a liquid sample containing an analyte therethrough, said container having a full diameter bed region and a reduced diameter bed region; b) within the passage in the reduced diameter bed region, a thin layer of microparticulate extraction media, wherein the extraction media layer has a top surface, a bottom surface, and a peripheral edge, and the extraction media layer is oriented in the passage so that liquid flows through the extraction media layer from its top surface to the bottom surface; c) an upper compression layer in the full diameter bed region having an effective diameter bed area, located at the top surface of the extraction media layer and a lower compression layer in the reduced diameter bed region, located at the bottom surface of the extraction media layer, the two compression layers pressing the extraction media therebetween, wherein the effective area of the of the extraction media is smaller than the effective area of the upper compression layer; and d) an upper mesh flow distributor above the upper compression layer for distributing flow of the liquid sample uniformly to the extraction media layer top surface.
2. The apparatus of embodiment 1, wherein the ratio between the effective area of the extraction media to the effective area of the upper compression layer is about 1:10.
3. The apparatus of embodiment 1 or embodiment 2, wherein the ratio between the effective area of the extraction media to the effective area of the upper compression layer is about 1:4.
4. The apparatus of any one of embodiments 1-3, wherein the extraction media has a number average particle size of about less than 20 μm.
5. The apparatus of any one of embodiments 1-4, wherein the extraction media has a small particle size having a number average particle size of less than about 40 microns, less than about 30 microns, less than about 25 microns, less than about 20 microns, less than about 15 microns, less than about 10 microns, or less than about 5 microns.
6. The apparatus of any of embodiments 1-5, wherein the extraction media comprises particles that are sorbent particles selected from ion exchange sorbents, reversed phase sorbents, and normal phase sorbents.
7. The apparatus of embodiment 6, wherein the sorbent particles are selected from an inorganic material such as $SiO_2$ or an organic polymeric material such as poly (divinylbenzene), silica based particles (such as silica based carboxylic acids), diatomaceous earth particles, polymeric based particles, mono-dispersed silica and polymeric particles, and/or carbon graphite particles.
8. The apparatus of embodiment 7, wherein the sorbent particles are treated with an organic functional group such as a $C_2$-$C_{22}$, preferably $C_8$-$C_{18}$, functional group.
9. The apparatus of any of embodiments 1-8, wherein the extraction bed comprises at least two different extraction media in a single bed.
10. The apparatus of any of embodiments 1-9, wherein the apparatus further comprises one or more additional extraction beds.
11. The apparatus of any of embodiments 1-10, wherein the extraction media is loosely packed or is compacted.
12. The apparatus of any of embodiments 1-11, wherein one or more of the compression layers is flat, spherical, a truncated cone, prismatic, or a truncated pyramid.
13. The apparatus of any of embodiments 1-12, wherein one or more of the compression layers has a pore size less than the particle size of the extraction media.
14. The apparatus of embodiment 13, wherein one or more of the compression layers has a pore size of less than 5 microns or less than 3 microns.
15. The apparatus of any of embodiments 1-14, wherein the compression layers are composed of a flexible, hydrophobic material.
16. The apparatus of embodiment 15, wherein the compression layer comprises a glass microfiber media and/or a polymer.
17. The apparatus of embodiment 15, wherein the compression layer comprises polypropylene or polyethylene.
18. The apparatus of any of embodiments 1-17, wherein the compression layer has a thickness ranging from about 0.1 mm to about 3.25 mm, about 0.25 mm to about 3.25 mm, about 0.5 mm to about 3.0 mm, about 0.75 mm to about 3 mm, about 0.25 mm to about 2.5 mm, about 0.25 mm to about 2 mm, about 0.25 mm to about 1.5 mm, about 0.25 mm to about 1.25 mm, about 0.25 mm to about 1.0 mm, about 0.1 mm to about 0.75 mm, or about 0.1 mm to about 0.5 mm.

19. The apparatus of any of embodiments 1-18, wherein the flow distributor is a flexible mesh material having a mesh number of 200 or higher.

20. The apparatus of any of embodiments 1-19, wherein the flow distributor comprises one or more of Polyphenelyne Sulfide (PPS), Polytetrafluoroethylene (PTFE), Polyether ether Ketone (PEEK), Polyoxymethylene (POM), Ethylene Propylene Diene (EPDM), a Fluorinated elastomer (FKM), a Perfluoro elastomer (FFKM), polysulfone (PSU), Ethylene Tetrafluoroethylene (ETFE), Polypropylene (PP), (Poly)Chlorotrifluoroethylene (PCTFE/CTFE), polystyrene, high density polyethylene, polycarbonate, nylon, polyethylene terephthalate (PET), silicon, rubber, or polyester.

21. The apparatus according to any of embodiments 1-20, further comprising a middle flow distributor below the upper compression layer and/or a lower flow distributor below the lower compression layer.

22. The apparatus according to embodiment 21, wherein the flow distributors are layered or molded in the housing above and below the compression layers.

23. The apparatus according to embodiment 22, wherein the upper flow distributor is located in the full diameter region and the lower flow distributor is seated in a lower portion of the apparatus, having a reduced diameter.

24. The apparatus according to any of embodiments 1-23, wherein the apparatus is configured for an elution volume of about 0.025 ml to about 0.25 ml, about 0.025 ml to about 0.2 ml, about 0.025 ml to about 0.15 ml, about 0.025 ml to about 0.100 ml.

25. The apparatus according to any of embodiments 1-24, wherein the entrance is configured to receive a connective fitting to connect the apparatus to a fluid input device.

26. The apparatus according to any of embodiments 1-25, wherein the fluid input device comprises automated fluid dispensing systems, automated liquid handling platforms, syringes, and microdispensers.

27. An extraction plate comprising multiple apparatuses according to any of embodiments 1-26.

28. The extraction plate according to embodiment 27, wherein the apparatuses are arranged in a multicolumn array.

29. An apparatus for extracting an analyte from a liquid sample comprising: a) a container having an entrance, an exit, and a passage therebetween for passage of a liquid sample containing an analyte therethrough, said container having a full diameter bed region and a reduced diameter bed region; and b) a layered construction having a top and a bottom extending across the passage, comprising from top to bottom: (i) an upper flow distributor/support layer, (ii) an upper compression layer, (iii) an extraction layer of microparticulate extraction medium adjacent to the layer (ii), and (iv) a lower compression layer located adjacent to the extraction layer (iii), wherein the (i) upper flow distributor and (ii) upper compression layer are located in the full diameter region, the (iii) extraction layer and (iv) lower compression layer are located in the reduced diameter region.

30. The apparatus of embodiment 29, wherein the full diameter region has an effective bed area measured by $A_F=\pi r_F^2$, where $r_F$ is the radius of an interior surface of the container in the full diameter region, and $A_r=\pi r_r^2$ where $r_r$ is the radius of an interior surface of the container in the reduced diameter region, and wherein the ratio between the effective bed area of the full diameter region and the effective area of the reduced diameter region ranges from about 10:1 to 1.5:1.

31. The apparatus of embodiment 29, wherein the ratio between the effective bed area of the full diameter region and the effective area of the reduced diameter region is about 4:1.

32. The apparatus of embodiment 29, wherein the layered construction having a top and a bottom extending across the passage, comprises from top to bottom: (i) an upper flow distributor, (ii) an upper compression layer, (i') a middle flow distributor, (ii') a middle compression layer in the reduced diameter region, (iii) an extraction layer of microparticulate extraction medium adjacent to the layer (ii'), (iv) a lower compression layer adjacent to layer (iii), and (v) optionally, a lower flow distributor, wherein layers (i), (ii), (i'), and (ii') are located in the full diameter region, and layers (iii)-(v) may be located in the reduced diameter region.

33. The apparatus of embodiment 29, wherein the layered construction having a top and a bottom extending across the passage, comprises from top to bottom: (i) an upper flow distributor, (ii) an upper compression layer, (i') a middle flow distributor, (ii') a middle compression layer in the reduced diameter region, (iii) an extraction layer of microparticulate extraction medium adjacent to the layer (ii'), (iv) a lower compression layer adjacent to layer (iii), and (v) optionally, a lower flow distributor, wherein layers (i), (ii), and (i'), are located in the full diameter region, and layers (ii')-(v) are located in the reduced diameter region.

34. The apparatus of embodiment 29, further comprising one or more air gap layer(s).

35. The apparatus of embodiment 34, wherein an air gap layer is located in the reduced-diameter region.

36. The apparatus of embodiment 35, wherein the air gap layer has a height that ranges from ½ the diameter of the reduced diameter region to 4 times the diameter of the reduced diameter region.

37. The apparatus of embodiment 33, further comprising an air gap layer located between layer (i') and layer (ii').

38. The apparatus of embodiment 37, wherein the air gap layer is located in the reduced diameter region.

39. The apparatus according to any of embodiments 34-38, wherein the air gap has a height range from about 0.5 to about 1 times, about 0.5 to about 1.5 times, about 0.5 to about 2 times, about % to about 2.5 times, about 0.5 to about 3 times, about 0.5 to about 3.5 times, about % to about 4 times, about 1 to about 1.5 times, about 1 to about 2 times, about 1 to about 2.5 times, about 1 to about 3 times, about 1 to about 3.5 times, about 1 to about 4 times, about 1.5 to about 2 times, about 1.5 to about 2.5 times, about 1.5 to about 3 times, about 1.5 to about 3.5 times, about 1.5 to about 4 times, about 2 to about 2.5 times, about 2 to about 3 times, about 2 to about 3.5 times, about 2 to about 4 times, about 2.5 to about 3 times, about 2.5 to about 3.5 times, about 2.5 to about 4 times, about 3 to about 3.5 times, about 3 to about 4 times, or about 3.5 to about 4 times, the diameter of the reduced diameter region.

40. The apparatus of any of embodiments 1-26 or embodiments 29-39, further comprising a tip region.

41. The apparatus according to embodiment 40, wherein the tip region is cylindrical or conical.

42. The apparatus according to embodiment 41, where in the tip region has the same diameter of the reduced diameter bed region or a smaller diameter bed than the reduced diameter bed region.
43. The apparatus according to any of embodiments 40-42, wherein the tip region is in the form of a luer tip.
44. A method for the extraction of an analyte from a sample comprising: a) contacting an apparatus or extraction plate of any of embodiments 1-43 with a sample in a liquid buffer, and b) eluting the sample from the apparatus with an elution buffer.
45. The method according to embodiment 44, further comprising one or more conditioning or washing steps before, during, or after contacting the apparatus with the sample.
46. A kit comprising an apparatus or extraction plate according to any of embodiments 1-43.
47. The kit according to embodiment 46, further comprising one or more elution buffers or wash buffers.

EXAMPLES

The following non-limiting examples are provided for illustrative purposes only in order to facilitate a more complete understanding of the disclosed subject matter. These examples should not be construed to limit any of the embodiments described in the present specification, including those pertaining to the apparatus used therein and the methods of using the present apparatus.

Example 1

Extraction of the Catecholamines from Plasma

Control Single diameter column: CEREX® WCX 1 cc 10 mg columns.

Present Apparatus "narrow bore column": The narrow bore column was a 1 cc column having an effective area ratio of 4:1 (full diameter to reduced diameter). The layers of the column were: (i) an upper flow distributor screen, (ii) a cylindrical fabric compression layer, (iii) a lower flow distributor screen, (iv) a spherical frit as a compression layer, (v) the microparticulate extraction medium, and (vi) a spherical frit as a lower compression layer. Layers (i)-(iii) were located in the full-diameter region, where layers (iv)-(vi) were located in the reduced diameter region. The extraction medium was the same as the extraction medium used in the CEREX® WCX 1 cc 10 mg columns.

Normal human serum samples were obtained from Bioreclamation Corp. and spiked with catecholamines prior to solid phase extraction. The blanks and plasma samples were also spiked with internal standards (e.g., dopamine-D4, epinephrine-D6, and norepinephrine-D6).

CEREX® WCX (1 cc/10 mg) (control and narrow bore) columns were conditioned with 0.5 ml of methanol, followed by 0.5 ml of 10 mM Phosphate Buffer pH 6.8.

0.5 mL 10 mM Phosphate buffer was mixed with 100 µL of the Sample. The Sample/buffer mix at a pH of 6.8 was loaded onto the column at a pressure of 2-3 psi. The column was washed with 1 mL deionized water at 6 psi and subsequently washed with 1 ml Acetonitrile at 6 psi.

Two sets of columns were loaded for each type of column. One half of the columns (control and narrow bore) were eluted with 0.5 mL of Elution Buffer—25:75 100 mM Potassium Carbonate:Acetonitrile. The other half of the columns were eluted with 0.1 mL of 25:75 100 mM Potassium Carbonate:Acetonitrile. 25 µL of the eluent was used loaded for the LC-MS/MS reaction.

Example 2

LC-MS/MS Analysis of the Catecholamines

25 µL of the solution obtained from the extraction was automatically injected into a TARGA® C18 3 µm particle size 50×2.1 mm analytical column. A binary HPLC gradient was applied to the analytical column to separate the epinephrine, norepinephrine and dopamine from other analytes contained in the sample. Mobile phase A was 5.0 mM ammonium formate with 0.1% formic acid pH 3.0 and mobile phase B was Acetonitrile with 0.1% formic acid. The HPLC gradient proceeded at a temperature of 35° C. with a flow rate of 500 µL/min over five minutes as follows:

|  | Time (min) | B (%) |
|---|---|---|
| Gradient: | 0.01 | 50 |
|  | 3.00 | 100 |
|  | 4.00 | 100 |
|  | 4.50 | 50 |
|  | 5.00 | 50 |

MS/MS was performed using an APPLIED BIOSYSTEMS MDS SCIEX 500®, although other suitable MS/MS apparatuses are known. The following software programs were used in the present examples: ANALYST 1.5.2®, although other suitable software systems are known. Liquid solvent/analyte exiting the analytical column flowed to the heated nebulizer interface of the MS/MS analyzer. The solvent/analyte mixture was converted to vapor in the heated tubing of the interface. Analytes in the nebulized solvent were ionized by heated ESI.

Ions passed to the first quadrupole (Q1), which selected ions with a mass to charge ratio of parent ions generated from one of the analytes. Ions entering quadrupole 2 (Q2) collided with argon gas to generate ion fragments, which were passed to quadrupole 3 (Q3) for further selection. After measurement of ions indicative of one of the analytes, Q1 was adjusted so that ions with a mass to charge ratio of parent ion from a second analyte were selected. These ions were collided with nitrogen gas in Q2, and the ion fragments passed to Q3 for further selection. After measurement of these ions, Q1 was adjusted so that ions with a mass to charge ratio of parent ion from a third analyte were selected. These ions were collided with argon gas in Q2, and the ion fragments passed to Q3 for further selection. Simultaneously, the same process using isotope dilution mass spectrometry was carried out with internal standards, dopamine-D4 and/or epinephrine-D6, and/or norepinephrine-D6. The following mass transitions were used for detection and quantitation of epinephrine, norepinephrine and dopamine (and their corresponding internal standards) during validation on positive polarity from the same sample injection.

Table 1 shows the data representing the percent recovery of catecholamines from a plasma sample spiked with 1 ng/ml catecholamine. Notably, the narrow bore columns performed significantly better for all catecholamines at all elution volumes. In particular, the small volume elution (i.e., the 0.1 ml elution) performed at least approximately three times as well as the small volume elution using the conventional column.

TABLE 1

Absolute Recovery Comparison at 1 ng/ml Plasma

| Compound | Cerex 10 mg 1 cc WCX column 0.5 ml elution | Cerex 10 mg 1 cc WCX column 0.1 ml elution | Cerex 10 mg 1 cc WCX Narrow Bore 0.5 ml elution | Cerex 10 mg 1 cc WCX Narrow Bore 0.1 ml elution |
|---|---|---|---|---|
| Dopamine | 98.3% cv = 8.3% | 27.6% cv = 11.5% | 99.5% cv = 4.6% | 99.6% cv = 4.4% |
| Dopamine-D4 | 96.8% cv = 9.8% | 32.4% cv = 10.4% | 99.5% cv = 4.2% | 98.6% cv = 4.7% |
| Epinephrine | 92.3% cv = 12.6% | 35.6% cv = 11.5% | 97.5% cv = 3.8% | 97.2% cv = 5.0% |
| Epinephrine-D6 | 91.4% cv = 12.8% | 38.5% cv = 13.2% | 96.7% cv = 4.1% | 98.1% cv = 4.5% |
| Norepinephrine | 87.3% cv = 14.3% | 15.6% cv = 22.5% | 93.0% cv = 5.8% | 92.1% cv = 6.2% |
| Norepinehrine-D6 | 85.6% cv = 15.2% | 13.9% cv = 23.0% | 91.5% cv = 5.4% | 90.9% cv = 5.7% |

As shown in the chromatograms of FIG. 4A-F and FIG. 5A-F, extracting and detecting catecholamine in plasma from healthy donors by using the present apparatus (i.e., the narrow bore column).

The chromatography demonstrates the sensitivity of the assay. The absolute recovery chart demonstrates the improved recovery and improved reproducibility using the narrow bore columns vs conventional columns.

Another benefit of the present apparatus is that due to the smaller elution volumes from the reduced effective bed diameter the present apparatus can collect into smaller vessels and eliminate transfers.

Example 3

Extraction of Buprenorphine and Norbuprenorphine from Urine

Narrow Bore Extraction columns feature high-capacity, high-efficiency, low bed mass sorbents that permit the use of low elution volumes (50-100 μL). These elution volumes lend themselves to evaporation within the positive pressure SPE processor unit such as an ALDIII™ or an IP8™ (SPEware Corp., Baldwin Park, Calif.), eliminating the need for a separate solvent evaporator. This allows the use of selective elution solvents, resulting in cleaner extracts than would be possible using high solvent strength (low specificity) elution solvents.

Buprenorphine and norbuprenorphine were chosen as model compounds for several reasons. They are frequently monitored as part of "pain panels" in compliance testing laboratories. Their relevant concentrations are relatively low and thus require low LLODs. Additionally, they are excreted in urine primarily as glucuronide conjugates, affording the opportunity to evaluate both solid phase extraction efficiency with narrow bore SPE columns.

Experimental

Reagents
a) water, b) negative control urine (diluent for the stand-ard curve), and c) a "master mix" containing 100 mM sodium ace-tate buffer pH 4.8, the internal standard solution (B-d4 and N-d3), and β-glucuronidase solution (2500 units/sample, catalog #BG100, red abalone, Kura Biotec, Inglewood, Calif.).

Process
A calibration curve was prepared from a single high calibrator via serial dilution. "Master mix" was placed in all wells of a 96-well incubation plate on the plate heater (preheated to 68° C.). Calibrators and controls (100 μL specimen volume) were then transferred to the incubator plate. After 15 minutes, the contents of the incubation plate were transferred to the 96-well SPE plate for extraction.

Solid Phase Extraction:

Apply samples to narrow bore extraction columns with PSCX sorbent (2.5 mg)

Wash w/250 μL deionized water

Wash w/150 μL 100 mM acetic acid

Wash w/300 μL methanol

Dry sorbent for 1 minute

Transfer the SPE plate to collection

Elute w/50 μL elution solvent (ethyl acetate:methanol:conc. NH4OH=93:5:2)

Dry the solvent

Dissolve residues in the reconstitution solvent (100 mL, aqueous formic acid 0.1%:methanol=80:20)

Analytical Conditions

Lc Conditions:

Column: Haisil C18 HL, 50×2.1 mm, 5 μM (Higgins Analytical, Inc., Mountain View, Calif.)

Flow: 400 μL/min

Injection volume: 10 μL

A=0.1% Aqueous formic acid; B=Methanol;

Gradient: 20-40% B in 0.5 min., 40-60% B in 2 min.

MS Conditions: Sciex 5000, Source=ESI; Positive ion MRM

Buprenorphine 468.25→55.10 (quant), 83.2 (qual)

Buprenorphine-d4 472.42→59.0 (quant), 83.0 (qual)

Norbuprenorphine 414.200→55.10 (quant), 83.0 (qual)

Norbuprenorphine-d3 417.01→54.8 (quant), 83.1 (qual)

Results and Conclusions

Figure 6A:
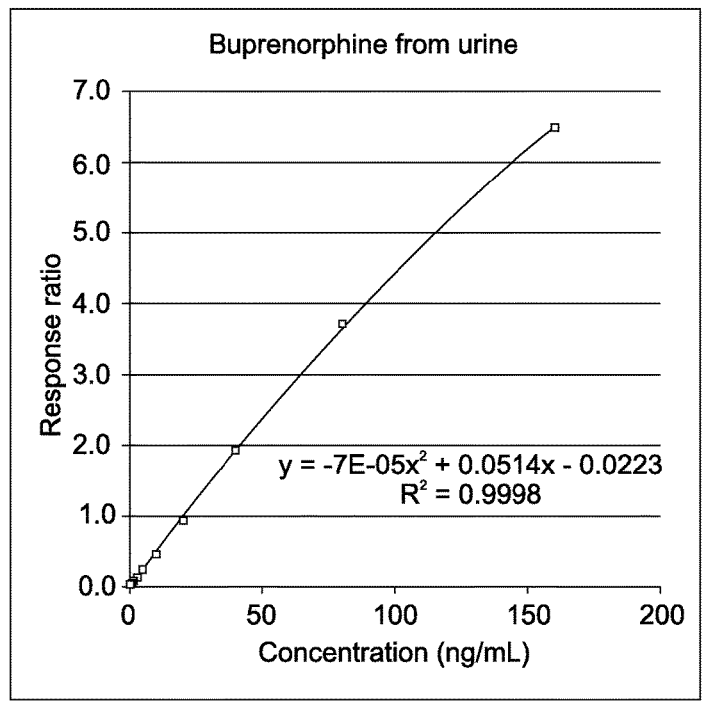
FIG. 6A is calibration curve of buprenorphine extracted from urine with the present apparatus.
Figure 6B:
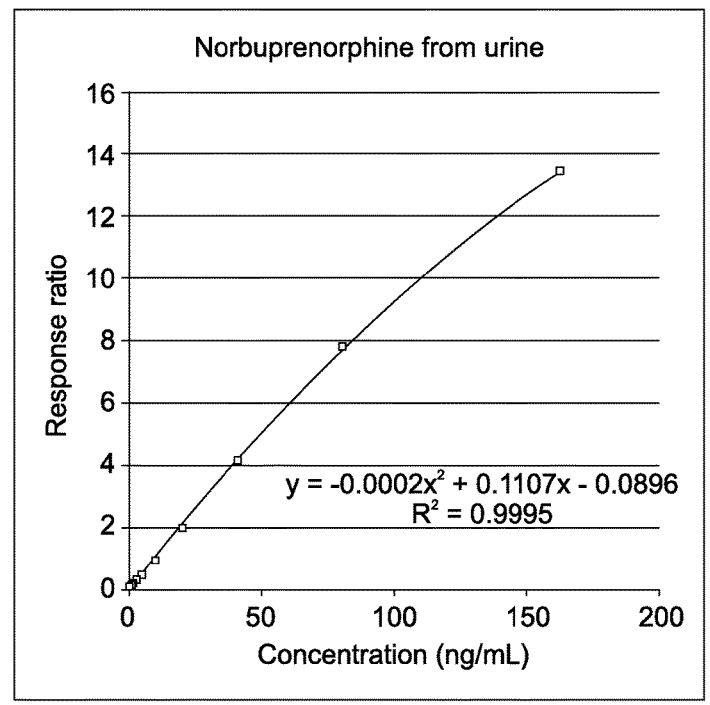
FIG. 6B is calibration curve of norbuprenorphine extracted from urine with the present apparatus.

Calibration curves for B and N are shown in FIG. 6. Regression is quadratic, 1/x weighted. Based on s/n ratios of the quantitation ions and assessment of curve accuracy (requiring ±20% from nominal value at the low calibrator), the LLOQs were determined to be 0.313 ng/mL and 0.625 for B and N, respectively.

Results from the analysis of non-validated control samples (n=10 each) are as follows:

TABLE 2

| | Burprenorphine | | | | | |
|---|---|---|---|---|---|---|
| | Buprenorphine | | Hydrolysis | | Hydrolysis | |
| | Low Control #1 0.75 ng/mL | Low Control #2 1.2 ng/mL | Control 5.0 ng/mL | Low Control #1 100 ng/mL | Low Control #2 150 ng/mL | Control 100 ng/mL |
| Average | 0.91 | 1.4 | 5.3 | 107 | 167 | 110 |
| Bias | 22% | 16% | 6% | 7% | 11% | 10% |
| CV (RSD) | 3.1% | 3.1% | 3.6% | 3.2% | 4.0% | 3.6% |

TABLE 3

| | Norbuprenorphine | | | | | |
|---|---|---|---|---|---|---|
| | Norbuprenorphine | | Hydrolysis | | Hydrolysis | |
| | Low Control #1 0.75 ng/mL | Low Control #2 1.2 ng/mL | Control 5.0 ng/mL | Low Control #1 100 ng/mL | Low Control #2 150 ng/mL | Control 100 ng/mL |
| Average | 0.97 | 1.4 | 4.7 | 106 | 165 | 103 |
| Bias | 29% | 16% | −6% | 6% | 10% | 3% |
| CV (RSD) | 3.5% | 4.0% | 4.8% | 2.7% | 4.0% | 5.6% |

RSDs were less than 5%. Absolute recoveries from urine using the Narrow Bore Extraction column with a 2.5 mg bed mass were 91% and 97% for B and N, respectively. The experiment was repeated with a urine sample supplemented with morphine at 20,000 ng per mL. No difference in absolute recovery was noted.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit.

At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. An apparatus for extracting an analyte from a liquid sample, the apparatus comprising:
    a container having an entrance, an exit, and a passage fluidly communicating therebetween for permitting flow of the liquid sample from the entrance to the exit, the container having a full diameter bed region nearest the entrance, a reduced diameter bed region between the full diameter bed region and the exit, and a tip region nearest the exit, a first shelf defined between the full diameter bed region and the reduced diameter bed region, and a second shelf defined between the reduced diameter bed region and the tip region;
    a first media assembly positioned within the full diameter bed region, the first media assembly seated on and contacting the first shelf, the first media assembly comprising a first flow distributor layer, a second flow distributor layer, and a first polypropylene frit layer, the first flow distributor layer is a polyethylene mesh flow distributor layer and the second flow distributor layer is a glass fiber layer; and
    a second media assembly positioned within the reduced diameter bed region, the second media assembly seated on and contacting the second shelf, the second media assembly comprising a second polypropylene frit layer, a third polypropylene frit layer and a microparticulate extraction media layer with sorbent properties sandwiched between the second polypropylene frit layer and the third polypropylene frit layer, the first media assembly and the second media assembly are spaced apart by a gap within the passage;
    wherein, in use, the container receives the fluid sample from the entrance, the fluid sample selectively flowing through the first media assembly and, thereafter, through the second media assembly, and flowing out of the container through the exit.

2. The apparatus of claim 1, wherein the gap is located in the reduced diameter bed region.

3. The apparatus of claim 1, wherein the gap is located completely within the reduced diameter bed region.

4. The apparatus according to claim 1, wherein the first polypropylene frit layer is positioned between the polyethylene mesh flow distributor layer and the glass fiber layer.

5. The apparatus according to claim 1, wherein the entrance selectively receives a connective fitting to connect the apparatus to a fluid input device.

6. The apparatus of claim 1, wherein a ratio between a full cross sectional internal area of the full diameter bed region and the reduced cross sectional internal area of the reduced diameter bed region ranges between 10:1 to 1.5:1.

7. The apparatus of claim 1 wherein the second media assembly further comprises a lower flow distributor, the lower flow distributor positioned atop the second shelf.

8. The apparatus of claim 1 wherein a plurality of the containers are arranged in an array which correspond to a collection plate with an array of wells.

9. An apparatus for extracting an analyte from a liquid sample, the apparatus comprising:
    a container having an entrance, an exit, and a passage fluidly communicating between the entrance and exit for permitting flow of the liquid sample therethrough, the container having a full diameter bed region opening to the entrance, a reduced diameter bed region opposite the entrance and in fluid communication with the full diameter bed region, and a tip region in fluid communication with the reduced diameter bed region and opening to the exit, a first shelf defined between the full diameter bed region and the reduced diameter bed region, and a second shelf defined between the reduced diameter bed region and the tip region;
    a first media assembly positioned within the full diameter bed region, the first media assembly seated on and contacting the first shelf, the first media assembly comprising a first flow distributor layer, a second flow distributor layer, and a first polypropylene frit layer, the first flow distributor layer is a polyethylene mesh flow distributor layer and the second flow distributor layer is a glass fiber layer;

a second media assembly positioned within the reduced diameter bed region, the second media assembly seated on and contacting the first shelf, the second media assembly comprising a second polypropylene frit layer, a third polypropylene frit layer and a microparticulate extraction media layer with sorbent properties sandwiched between the second polypropylene frit layer and the third polypropylene frit layer; and an air gap defined by the first media assembly being spaced apart from the second media assembly.

10. The apparatus of claim 9, wherein the air gap is located completely within the reduced diameter region.

11. The apparatus according to claim 9, wherein the first polypropylene frit layer is positioned between the polyethylene mesh flow distributor layer and the glass fiber layer.

12. The apparatus of claim 9 wherein a plurality of the containers are arranged in an array which correspond to a collection plate with an array of wells.

13. An apparatus for extracting an analyte from a liquid sample, the apparatus comprising:

a container having an entrance, an exit, and a passage fluidly communicating between the entrance and exit for permitting flow of the liquid sample therethrough, the container having a full diameter bed region opening to the entrance, a reduced diameter bed region opposite the entrance and in fluid communication with the full diameter bed region, and a tip region in fluid communication with the reduced diameter bed region and opening to the exit;

a first media assembly positioned within the full diameter bed region, the first media assembly comprising a first flow distributor layer, a second flow distributor layer, and a first polypropylene frit layer, the first flow distributor layer is a polyethylene mesh flow distributor layer and the second flow distributor layer is a glass fiber layer;

a second media assembly positioned within the reduced diameter bed region, the second media assembly comprising a second polypropylene frit layer, a third polypropylene frit layer and a microparticulate extraction media layer with sorbent properties sandwiched between the second polypropylene frit layer and the third polypropylene frit layer; and a gap defined between the first media assembly and the second media assembly.

14. The apparatus according to claim 13, wherein the first polypropylene frit layer is positioned between the polyethylene mesh flow distributor layer and the glass fiber layer.

15. The apparatus according to claim 13, wherein the gap is located in the reduced diameter bed region.

16. The apparatus according to claim 13, wherein a first shelf is defined between the full diameter bed region and the reduced diameter bed region, and a second shelf defined between the reduced diameter bed region and the tip region.

* * * * *